United States Patent [19]

Brentz

[11] Patent Number: 5,463,895
[45] Date of Patent: Nov. 7, 1995

[54] SAMPLE PIPETTING METHOD

[75] Inventor: Charles W. Brentz, Evanston, Ill.

[73] Assignee: Abbott Laboratories, Abbott Park, Ill.

[21] Appl. No.: 222,501

[22] Filed: Apr. 4, 1994

Related U.S. Application Data

[63] Continuation of Ser. No. 39,350, filed as PCT/US91/08375, Nov. 8, 1991, abandoned, which is a continuation-in-part of Ser. No. 612,160, Nov. 9, 1990, abandoned.

[51] Int. Cl.$^6$ ................................................. G01N 15/00
[52] U.S. Cl. ........................................................... 73/61.71
[58] Field of Search ........................... 73/61 R, 61.1 R, 73/290 R, 291 R, 863.01, 864.01, 61.41, 61.47, 61.71, 61.78, 61.73, 441, 438

[56] References Cited

U.S. PATENT DOCUMENTS

| | | | |
|---|---|---|---|
| 2,040,042 | 5/1936 | Eckstein | 73/61.73 |
| 2,986,924 | 6/1961 | Becker | 73/37.5 |
| 3,415,268 | 12/1968 | Tweed | 173/209 |
| 3,444,737 | 5/1969 | Jago | 73/290 |
| 3,474,902 | 10/1969 | Putman . | |
| 3,494,191 | 2/1970 | Cawley et al. . | |
| 3,661,191 | 5/1972 | Harley et al. | 141/41 |
| 3,712,136 | 1/1973 | Monsen | 73/290 |
| 3,735,636 | 5/1973 | Burke | 73/290 |
| 3,900,290 | 8/1975 | Hornstra . | |
| 4,140,018 | 2/1979 | Maldaelli et al. | 73/423 |
| 4,161,188 | 7/1979 | Jorgensen | 137/386 |
| 4,211,249 | 7/1980 | Richards | 137/393 |
| 4,228,831 | 10/1980 | Kerns | 141/27 |
| 4,241,606 | 12/1980 | Vandenhoeck | 73/290 |
| 4,452,899 | 6/1984 | Alston | 436/46 |
| 4,515,178 | 5/1985 | Campau | 137/393 |
| 4,555,957 | 12/1985 | Frankel et al. | 73/864.14 |
| 4,586,546 | 5/1986 | Mezei et al. | 141/2 |
| 4,591,568 | 5/1986 | Banno et al. | 436/180 |
| 4,715,413 | 12/1987 | Backlund et al. | 141/94 |
| 4,736,638 | 4/1988 | Okawa | 73/864.24 |
| 4,780,833 | 10/1988 | Atake . | |
| 4,794,085 | 12/1988 | Jessop et al. . | |
| 4,803,050 | 2/1989 | Mack | 422/65 |
| 4,846,003 | 7/1989 | Marquiss | 73/864.24 |
| 4,864,856 | 9/1989 | Ichikawa et al. | 73/290 |
| 4,893,515 | 1/1990 | Uchida | 73/864.34 |
| 4,944,922 | 7/1990 | Hayaski | 422/100 |
| 5,008,082 | 4/1991 | Shaw | 422/65 |
| 5,013,529 | 5/1991 | Itoh | 422/100 |

FOREIGN PATENT DOCUMENTS

| | | |
|---|---|---|
| 0273128 | 6/1988 | European Pat. Off. . |
| 0341438 | 11/1989 | European Pat. Off. ........ G01F 23/14 |

*Primary Examiner*—R. Raevis
*Attorney, Agent, or Firm*—Mark C. Bach

[57] ABSTRACT

A non-invasive method of determining the level of fluid present in a test sample. The level of fluid present in a test sample in a container is determined by moving a pipettor toward the sample surface while aspirating air and monitoring the pressure change produced with a sensor. Non-homogeneity of the sample can be detected during the aspiration of the sample using the invention.

5 Claims, 3 Drawing Sheets

SAMPLE PIPETTING METHOD

This application is a continuation of application Ser. No. 08/039,350 filed as PCT/US91/08375, Nov. 8, 1991, now abandoned, which is a continuation-in-part application of U.S. Ser. No. 07/612,160, filed Nov. 9, 1990, now abandoned.

BACKGROUND OF THE INVENTION

This invention relates generally to a non-invasive automated pipetting method, and more particularly, relates to determining the level of fluid present in a test sample. Level sensing is accomplished by moving a pipettor toward a sample while aspirating air and monitoring for a pressure change within the pipettor. Controlled aspiration of the fluid sample is then performed.

Automated pipetting systems that contact a liquid test sample with an electrode are known. For example, a conducting pipette tip or an electrode adjacent to the pipette tip generates an electrical signal when the conducting pipette tip or the electrode touches the surface of an electrically conducting fluid, such as a buffer solution or serum, plasma or urine sample. These methods involve invasive procedures which suffer from the danger of cross-contamination between test samples. A portion of the first sample clings to the pipette tip or electrode and the next sample to be pipetted becomes contaminated with the first sample when the pipette tip or electrode contacts the second sample. This cross-contamination or carry-over can also occur between assay reagents and between assay reagents and samples. The danger of cross-contamination or carry-over can be reduced by extensive washing of the pipette tip or electrode between each pipetting step, but such washing steps suffer from decreased sample throughput on the automated instrument.

Detecting the surface of a fluid is very important for the precise pipetting of the fluid. Locating the fluid surface permits the controlled immersion of the pipette tip in the fluid. By controlling the depth of immersion of the pipette tip in the fluid, a consistent amount of fluid will cling to the outside of the tip resulting in greater consistency in the total volume dispensed. The use of non-invasive fluid sample surface sensing methods and devices in conjunction with disposable polymeric pipette tips results in such greater control and consistency. Thus, non-invasive fluid sample surface sensing achieves two advantages. First, it eliminates the need to wash the pipette tip between sampling, thereby increasing the through put of the instrument. Second, a non-invasive surface probing method eliminates the potential of sample carry-over.

A non-invasive fluid surface-sensing system were disclosed in U.S. Pat. Nos. 3,474,902 and 3,494,191. This non-invasive fluid surface-sensing system utilizes a method that involves blowing air via a stepper-motor controlled syringe to detect a fluid surface level. This level sensing method can be used in automated pipetting of biological samples. However, air is often blown into the test sample causing bubbles and generating aerosols. In an attempt to minimize bubble creation, the pipettor is moved toward the sample very slowly until the sample surface is detected, and then immediately withdrawn to the end of its travel range. The syringe is then fully dispensed to blow all the remaining air out of the syringe. Finally, the pipettor is returned to the fluid surface and aspiration is commenced.

An object of the present invention is to non-invasively level sense a fluid sample without the need of blowing air through the pipette tip. Another object of the present invention is to aspirate a fluid sample by immersing the pipette tip into the sample at a controlled, minimal depth in order to minimize the amount of sample that clings to the outside of the pipette tip. Yet another object of the present invention is to detect nonhomogeneity, such as clots, bubbles and foam, in the fluid sample. Still other objects of the present invention will be apparent to one skilled in the art.

The present invention offers advantages over known methods of level sensing and aspiration of a fluid sample. Carry-over or cross-contamination between samples and reagents is eliminated by employing a non-invasive method in which no contact is made between the level sense means, such as a pressure transducer, and the test sample. The present invention also has advantages over positive pressure (blowing air) level sense methods. The possibility of bubbles and aerosols is eliminated by the present invention. Also, because the need to reverse the direction of the syringe pump between the level sense step and the aspiration step is eliminated, the instrument throughput is increased. In addition, the present invention eliminates the necessity of withdrawing the pipettor from the sample in order to evacuate the syringe before aspiration again improving the instrument throughput through the elimination of method steps without the creation of bubbles and aerosols.

SUMMARY OF THE INVENTION

This invention provides an apparatus and method of pipetting a fluid from a container, which comprises (a) determining the level of the fluid in the container by (i) determining the ambient air pressure within a pipettor as a baseline pressure reading, (ii) aspirating air into the pipettor as the pipettor moves toward the fluid sample in the container, (iii) monitoring for an air pressure change in the pipettor to indicate the surface level of the fluid in the container; (b) immersing the pipettor in the fluid and aspirating fluid from the container into the pipettor in controlled steps while aspirating incremental volumes; (c) monitoring pressure changes after each incremental aspiration step; and (d) moving the tip of the pipettor from the sample in such a way to shear off any droplets. The tip of the pipettor may be disposable or reusable.

The invention also provides an apparatus and method of detecting non-homogeneity in a fluid sample, such as the presence of foam or bubbles on the surface of the sample, and/or the presence of clots on the surface or in the bulk of the test sample. This method comprises (a) determining the ambient air pressure within a pipettor as a baseline pressure reading; (b) aspirating air into the pipettor as the pipettor moves towards a sample in a container; (c) monitoring for an air pressure change in the pipettor to indicate the surface level of the fluid in said container; (d) immersing the pipettor in the fluid and aspirating a volume of fluid from the container into the pipettor; (e) monitoring pressure changes after said aspiration of step (d); (f) comparing measured pressure change to predetermined normal aspiration pressure windows; and (g) observing pressure values falling outside said predetermined values.

DESCRIPTION OF PREFERRED EMBODIMENT

The novel level sensing and aspiration apparatus and method of the present invention is based upon measurable pressure changes within a pipettor during the level sensing and aspiration steps. When compared to conventional level sensing and aspiration apparatuses and methods, the present invention was surprisingly found to more rapidly and accurately level sense and aspirate a fluid sample.

Figure 6A:
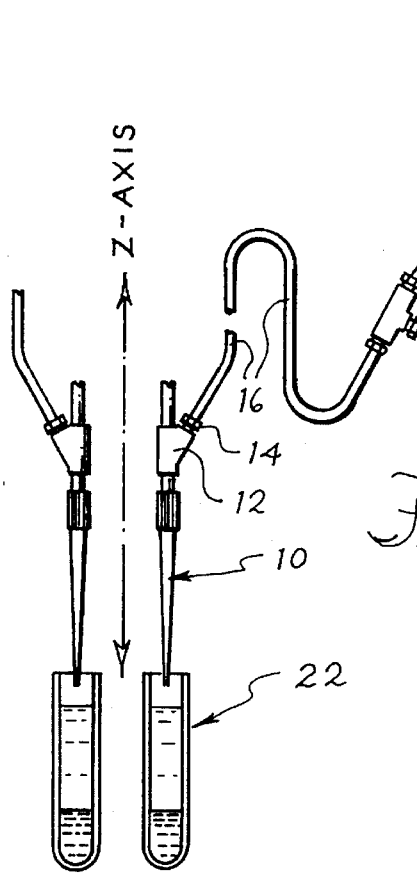
FIGS. 6a and FIG. 6b are illustrations of an apparatus which level senses and aspirates two samples simultaneously followed by dispensing of the two samples into a sample reaction tray.
Figure 6B:
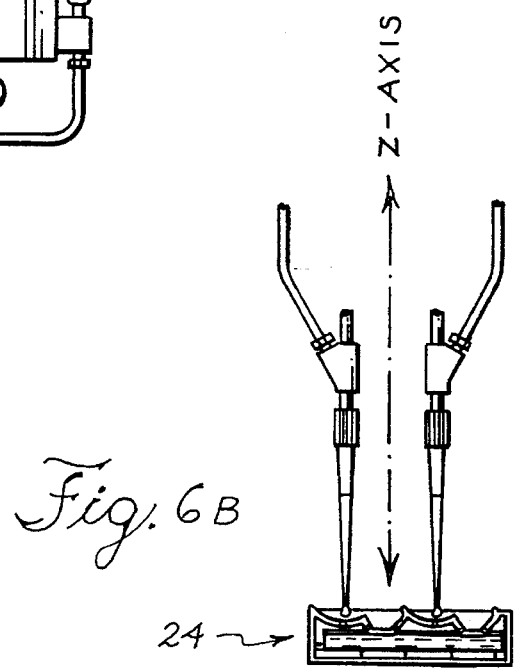

As illustrated in FIGS. 6a and 6b, the pipettor apparatus of the present invention is comprised of a disposable pipette tip 10 capable of making an air tight connection with a pipette tip holder means 12 having a bore and a tube connection means 14 capable of making an air tight coupling between tubing 16 and the pipettor such that air can be drawn through the disposable pipette tip 10 into the pipette tip holder means 12 and then into tubing 16. Tubing 16 is connected to a pressure measurement means 18 and a means 20 for aspirating air through the pipettor such that said connections are air tight. Finally, pipette tip holder means 12 is attached to a means (not shown) for moving the pipettor vertically along the Z-axis.

Pipette tip holder means 12 are well know in the art. For example, manual and automated pipettors are readily available which have a tip probe that permits the formation of an air tight seal between the pipettor and a disposable pipette tip and at the same time, permit the easy removal of the disposable pipette tip. In addition, a limit-switch can be incorporated to detect the presence or absence of a pipette tip on the tip probe, One skilled in the art would be able to prepare such a pipettor without undo experimentation. Also, tube connection means 14 are well known in the art, such as luer-lock, compression fitting tube adaptors and the like, and can be readily adapted by one skilled in the art for use in the present invention without undo experimentation.

Standard disposable pipette tips (10), such as polypropylene and the like, and standard tubing (16), such as Tygon®, vinyl, polypropylene, polyethylene, metal and the like, can be used in the present invention and are readily available for purchase. The disposable pipette tips (10) can be stored in racks which are accessible by the pipettor.

Pressure measurement means 18 measures the air pressure within the pipettor either continuously or periodically during the invention method. A preferred pressure measurement means is a pressure transducer (electrode). The pressure transducer is interfaced to a host computer system through a Datem dcm300 Digital I/O Board (available from Datem Limited, Ontario, Canada). The pressure transducer provides a 10-bit binary output (0 to 1023) with an ambient air pressure measuring at approximately the center of the range (512). Full scale pressure (+1 psi) translates to 0 and full scale vacuum (−1 psi) translates to 1023.

Means 20 for aspirating air through the pipettor must be capable of precisely controlled movements. For example, during level sense, the aspiration means (20) must be capable of stopping immediately after the pipette tip reaches the fluid surface. A preferred aspiration means (20) is a syringe, preferably a 1500 μL syringe, mechanically connected to a stepper motor and home limit-switches capable of controlling the movement of the syringe piston and causing the syringe to aspirate and dispense air through tubing 18. The stepper motor and home limit-switches are interfaced to the host computer through the Datem dcm340 Stepper Motor Control (available from Datem Limited, Ontario, Canada).

Means for moving the pipettor vertically along the Z-axis is an electro-mechanical assembly that is capable of at least moving the pipettor along the Z-axis (vertically) relative to the XY-plane of the sample container (22) and may also be capable of moving the pipettor along the X and Y axes. Preferably, a stepper-motor and home limit-switches are used for positioning the pipettor along the Z-axis. Again, the stepper-motor and home limit-switches are interfaced to the host computer through the Datem dcm340 Stepper Motor Control. Preferably, a Magnon XY Table (available from Magnon Engineering, Fontana, Calif.) or the like is used for positioning the pipettor. The Magnon XY Table includes both the mechanical hardware and the electronic controls necessary for positioning the pipettor. A Bitbus communication port (available from Intel, Santa Clara, Calif.) is used to interface the XY table controller to the host computer.

Multiple pipettor assemblies can be interfaced in order to pipet multiple samples simultaneously. For example, FIGS. 6a and 6b illustrates dual pipettor assemblies. Each pipettor assembly comprises a disposable pipette tip 10, pipette tip holder means 12 connected through tubing 16 to a pressure measurement means 18 and an aspiration means 20. The two pipettor assemblies are .interfaced with a means for moving both pipettors vertically along the Z-axis such that two samples can be level sensed and aspirated simultaneously or sequentially. These dual pipettor assemblies permit the dispensing of two samples into a reaction tray having dual reaction wells (24).

SAMPLE PIPETTING METHOD

The sample pipetting method of the present invention involves level sensing of the sample's fluid surface and sample aspiration. The following is a detailed summary of the present invention using the pipettor apparatus shown in FIG. 6:

LEVEL SENSE

1. The ambient air pressure is measured in the pipettor by a pressure transducer while the syringe is in its fully dispensed position and the pipettor is located at the top of its stroke in the Z axis. The value becomes a baseline to which all other pressure readings are compared. By using this value as a baseline, any effect on the pressure measurements due to changes in the atmospheric pressure are eliminated.

2. The pipettor is moved down toward the test sample until the pipette tip is even with the top of the test sample tube.

3. The pipettor is then moved downward toward the sample fluid surface. Simultaneously with the pipettor's movement down toward the sample fluid surface, air is aspirated through the pipettor by drawing air into the syringe and the pressure inside the pipettor is measured with the pressure transducer. Inherently in the process of aspirating air into the pipettor, the pressure in the pipettor will be measurably lower than ambient pressure.

4. When the pressure inside the pipettor suddenly drops, the tip of the pipettor has contacted the surface of the sample (see FIG. 1). Immediately, the movement of both the syringe and the pipettor is stopped. Preferably, the pipettor must be stopped so that the tip of the pipettor is not more than 0.125 or ⅛ inch below the surface of the sample. By stopping within 0.125 inches, the amount of sample fluid clinging to the outside of the pipette tip can be more easily minimized.

Figure 1:
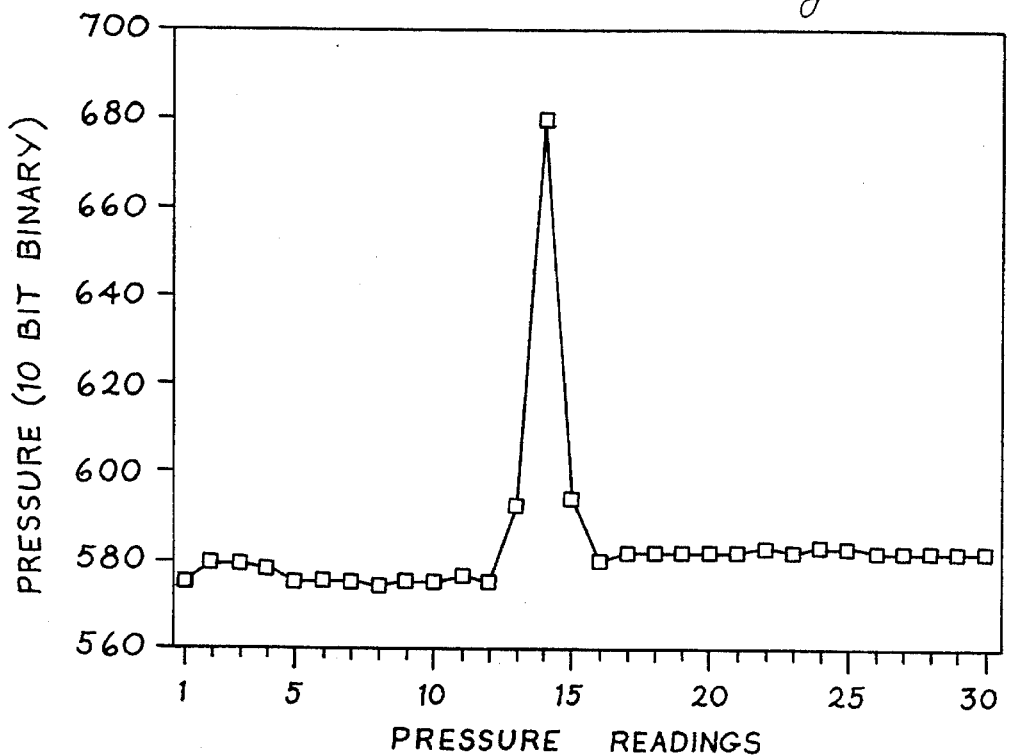
FIG. 1 is a graph of a representative sample of normal calf serum using the level sensing method of this invention wherein Pressure (+1 psi to −1 psi represented as 10 bit binary) is plotted against a sequential number of pressure readings taken at periodic intervals. The change in pressure occurs as the pipette tip touches the surface of the sample and the air aspiration is immediately halted.

The continuous pressure measurement will actually be recorded as a series of periodic measurements rather than one continuous measurement (see FIG. 1). It is well known that inherently, a pressure measurement system, such as described herein, must process the measured pressure value to record the value in a binary output and such data processing requires a minimum amount of time. Thus, the pressure is recorded shortly after each data processing cycle.

SAMPLE PIPETTING

5. The pipettor is lowered further into the, sample a short distance (approximately 0.055 inches) to avoid starving the pipettor of sample during sample aspiration.

Figure 2:
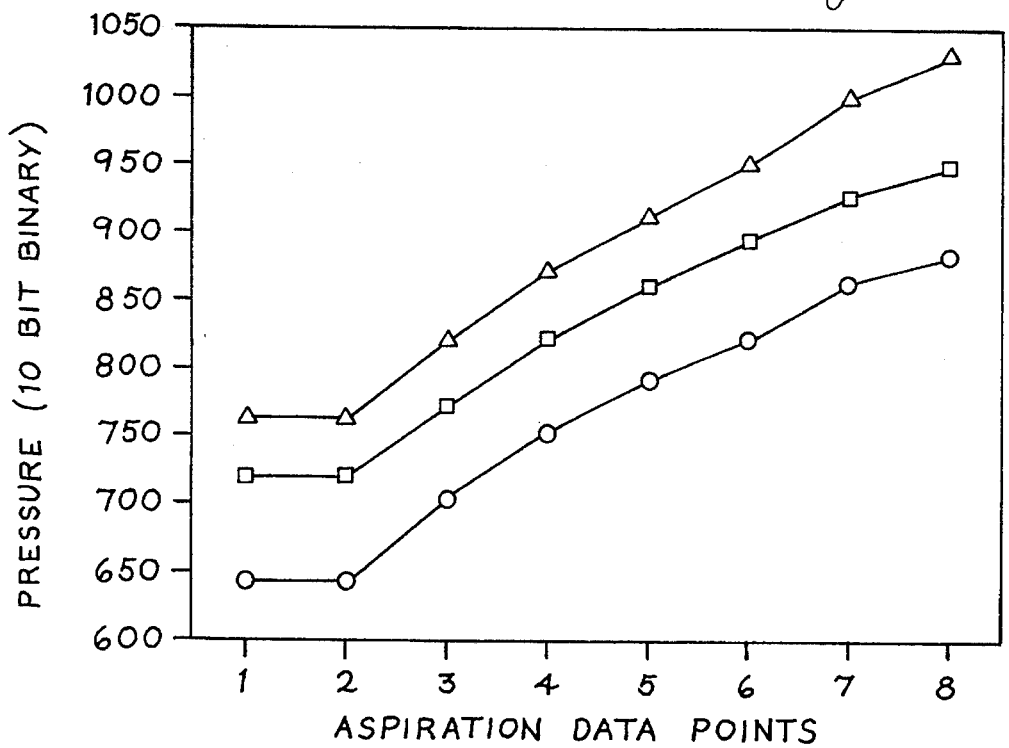
FIG. 2 is a graph of representative pressure changes during aspiration of a sample of normal calf serum using the level sensing and aspiration method of this invention to aspirate 1000 μL of sample, wherein Pressure (+1 psi to −1 psi represented as 10 bit binary) is plotted against Aspiration Data Points. All of the pressure measurements are within the predetermined aspiration pressure windows indicating a homogeneity in the sample.

6. At least about 100 μL of sample is aspirated into the pipettor by withdrawing the syringe the appropriate distance. Immediately after the syringe has stopped moving, the pressure in the pipettor is measured (see FIG. 2, Aspiration Data Point 1). The pressure is again measured after the pressure has reached equilibrium, i.e. a steady state pressure (about 0.2 seconds) (see FIG. 2, Aspiration Data Point 2).

Figure 3:
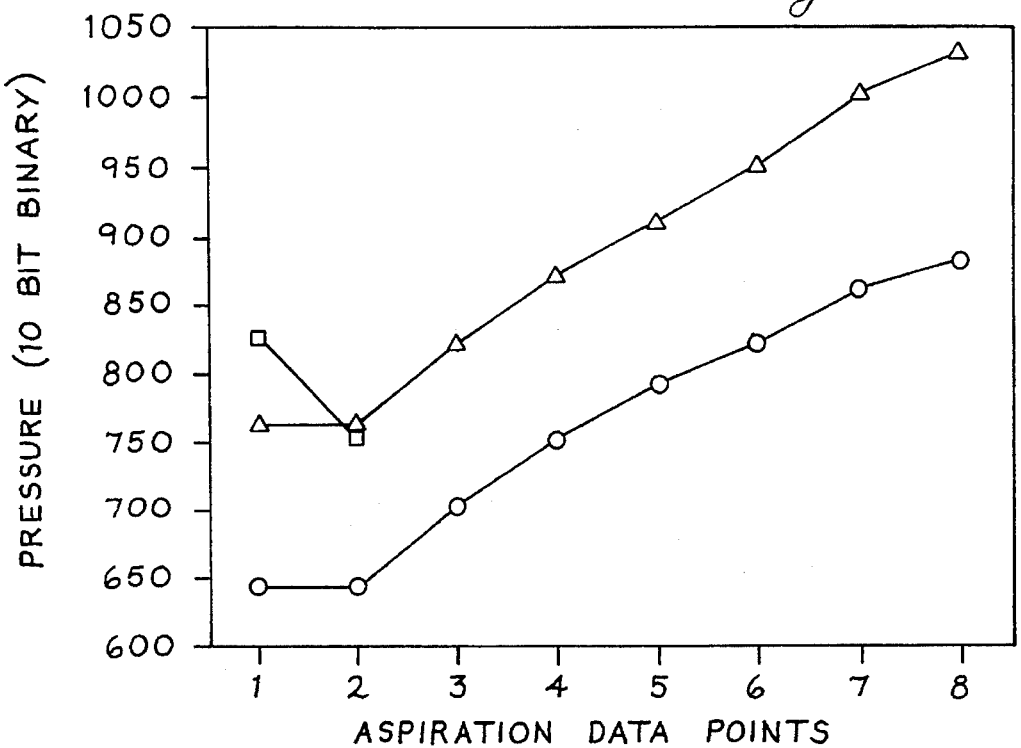
FIG. 3 is a graph of a representative sample of normal calf serum containing foam on the surface using the fluid level sensing and aspiration method of this invention to aspirate 1000 μL of sample, wherein Pressure (+1 psi to −1 psi represented as 10 bit binary) is plotted against Aspiration Data Points. At least one of the measured pressure values is outside a predetermined aspiration pressure window indicating a heterogeneity in the sample, i.e. the presence of foam.
Figure 4:
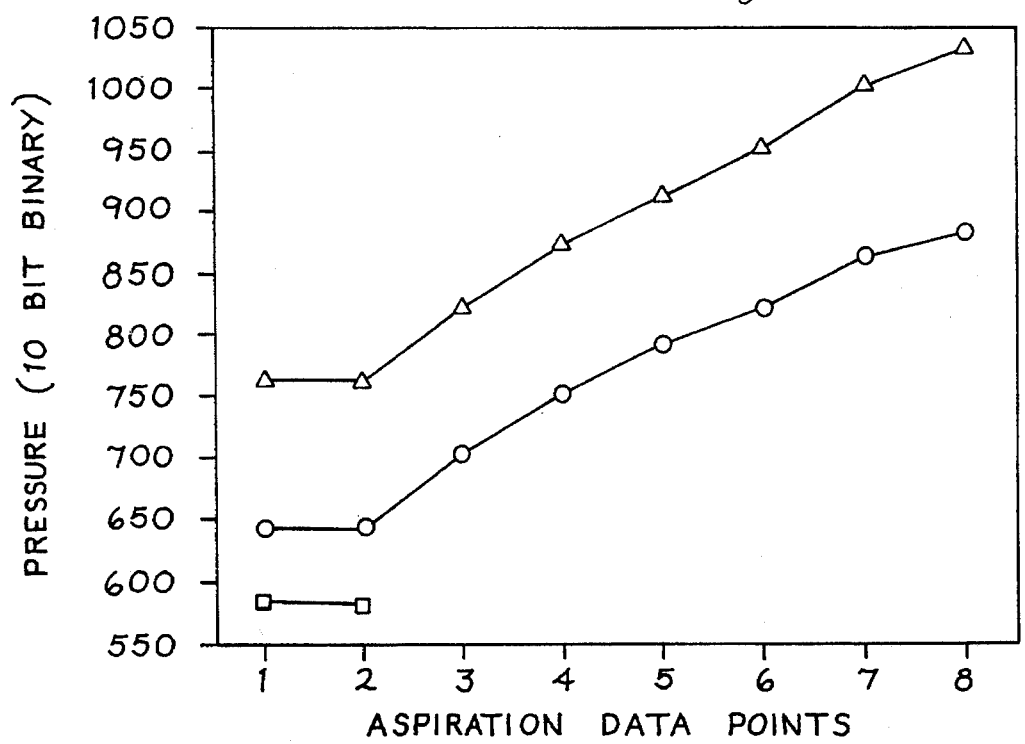
FIG. 4 is a graph of a representative sample of normal calf serum containing large bubbles on the surface using the fluid level sensing and aspiration method of this invention to aspirate 1000 μL of sample, wherein Pressure (+1 psi to −1 psi represented as 10 bit binary) is plotted against Aspiration Data Points. At least one of the measured pressure values is outside a predetermined aspiration pressure window indicating a heterogeneity in the sample, i.e. the presence of bubbles.

7. The two pressure measurement values are then compared with the aspiration pressure windows. If either or both pressure values, are outside the windows, the sample is nonhomogeneous and the pipetting is halted (see FIGS. 3–5): If the both values are within the windows, the pipetting is Continued with Step 8.

The aspiration pressure windows are calculated from the ambient pressure measurement taken in Step 1 above by adding empirically determined values to the ambient pressure measurement (see Table 1). The empirically determined values are obtained using standard experimental methods known in the art, i.e. a variety of normal, homogeneous samples are pipetted using the sample pipetting method herein with a variety of pressure transducers. Pressure transducers are known to differ in their individual performance characteristics and by establishing a normal range, i.e. aspiration pressure windows, variations between different transducers and between different normal samples can be eliminated from being a factor in the sample pipetting method. A nonhomogeneous sample is a sample that has at least one pressure measurement that falls outside the aspiration pressure windows which are the ranges within which the pressure measurements of normal, homogeneous samples will fall.

The empirically determined values are simply obtained by subtracting the ambient pressure (at the time of the normal sample pressure measurements) from the highest and lowest pipettor pressure measurements obtained during the sample pipetting of the normal samples. Thus, these empirical values when added to the ambient pressure in some future sample pipetting will automatically be adjusted for any variation in the ambient pressure at the time of the future sample pipetting.

8. The pipettor is then lowered further into the sample a short distance (approximately 0.055 inches) to avoid starving the pipettor of sample during sample aspiration.

9. About 150 μL of sample is aspirated into the pipettor by withdrawing the syringe the appropriate distance. The pressure in the pipettor is measured after the pressure has reached equilibrium, i.e. a steady state pressure (about 0.2 seconds) (see FIG. 2, Aspiration Data Point 3).

10. The pressure measurement value is then compared with aspiration pressure windows. If at least one pressure value is outside the corresponding window, the sample is nonhomogeneous and the pipetting is halted. If the value is within the windows, the pipetting is continued with Step 11.

11. Steps 8–10, i.e. an aspiration cycle (see FIG. 2, Aspiration Data Points 4–8), are repeated, if necessary, until the total desired amount of sample is aspirated into the pipettor (from about 100 μL to about 1000 μL).

12. The pipettor is moved up a short distance (approximately 0.055 inches) such that the pipettor tip is at the current sample surface. About 50 μL of sample is dispensed into the sample to eliminate any backlash in the syringe prior to dispensing the test sample into a reaction vessel. This backlash is well known to occur in mechanical systems due to looseness in the parts or imperfect gear meshing. Thus, as the mechanical system is moved in the reverse direction in order to move the syringe in the reverse direction, the backlash or slack in the system must be taken up before the syringe will begin moving. By dispensing about 50 μL of sample back into the sample tube, the backlash is removed and the dispensing of the sample into the reaction vessel will be more accurate.

13. The pipettor is then moved slowly up about 0.5 inches to prevent shearing off of a small amount of sample from inside the pipettor tip. The pipettor is then moved to the home position from which the pipettor can be moved to a dispensing location and is ready to dispense an accurate amount of sample into a reaction vessel.

In the level sensing method, the pipettor is moved downward toward the fluid sample's surface simultaneously with aspiration of air into the pipettor. Preferably, the syringe used in this method is a 1500 µL syringe. When using a 1500 µL syringe to aspirate 1000 µL of sample, only 500 µL is available for level sensing. Thus, the pipettor's movement down to the sample's surface must be coordinated with the 500 µL of air aspiration. The preferred syringe speed for the level sensing method is 160 µL per second and the speed of the pipettor is adjusted so that the pipettor reached the end of its stroke (i.e. the limit of the pipettor's downward movement) simultaneously with the syringe reaching 500 µL of air aspirated if no sample surface was detected. However, the pipettor's downward speed should preferably be less than the maximum speed so that the pipettor can be stopped such that the end of the pipette tip is no more than 0.125 (⅛) inch below the surface of the sample. The syringe begins aspiration prior to the downward movement of the pipettor from the point where the pipette tip is even with the top of the sample container. The delay in the pipettor's movement, preferably for about 0.2 seconds, gives the air pressure time to reach steady state.

The aspiration method begins after the sample surface has been level sensed and the pipette tip is located no more than about 0.125 inches below the sample's surface. Both the syringe and the pipettor are stationary. The pipettor is moved down a short distance, preferably about 0.055 inches, to prevent the pipettor from being starved for sample during aspiration. If the pipettor is starved for sample, air will be aspirated along with sample and an erroneous amount of sample will have been aspirated. At least 100 µL of sample is then aspirated (first aspiration). It is believed that about 100 µL of sample is the minimum amount of sample that can be accurately aspirated by this protocol using the apparatus shown in FIG. 6a and 6b. This amount of sample provides a consistent basis for comparison between various samples which permits the detection of non-homogeneity in a sample, such as bubbles, foam and the like, and other problems with the system, such as air leaks in the apparatus and the like.

Immediately after the syringe stops during the first aspiration of the sample, a pressure reading is taken (Aspiration Data Point 1). If this pressure reading is outside the aspiration pressure window for Aspiration Data Point 1, the sample is non-homogeneous. For example, a sample with high viscosity, such as a sample with clots or thick foam, will cause a higher vacuum to be created within the pipettor than a normal homogeneous sample. A sample with bubbles or a leak in the system will result in a lower vacuum within the pipettor than a normal homogeneous sample and may even read at ambient pressure. A second aspiration pressure reading (Aspiration Data Point 2) is taken within the pipettor after a short delay, preferably at least about 0.2 seconds, which is sufficient time for the pressure within the pipettor to reach a steady state. As with the first pressure reading, a pressure reading outside the aspiration pressure window corresponding to Aspiration Data Point 2 is an indication of non-homogeneity or problems with the system. Whenever any pressure reading is outside the corresponding aspiration pressure window, the aspiration process is stopped automatically.

The remainder of the sample that is to be aspirated into the pipettor is accomplished by sample aspiration cycles wherein a set volume (or less if that is all that is needed to obtain the desired amount of total sample aspirated), preferably at least about 100 µL, is aspirated in each cycle. More preferably, a volume of about 150 µL is aspirated during each aspiration cycle. Thus, seven aspiration cycles would be needed to completely aspirate a total of 1000 µL of sample. An aspiration cycle includes the following: (1) moving the pipettor downward into the sample a short distance, preferably about 0.055 inches, in order to avoid starving the pipettor of sample; (2) aspirating a volume of sample into the pipettor, preferably about 150 µL; and (3) after a short delay, preferably at least about 0.2 seconds, taking a pressure reading within the pipettor (Aspiration Data Points 3–8). Again, if a pressure reading is outside the corresponding aspiration pressure window, the sample is non-homogeneous and the aspiration is stopped.

The aspiration pressure windows are empirically derived values. A number of normal homogeneous fluid samples are aspirated using the present invention method using different lots of pressure measurement means. Thus, the normal fluctuations in the pressure readings (Aspiration Data Points) due to variations in the samples and pressure measurement means will establish a normal range of pressure values that can be expected to be observed when aspirating normal homogeneous samples. The range at each Aspiration Data Point extends from the lowest pressure reading value to the highest pressure reading value obtained when the normal homogeneous samples were aspirated. To eliminate the effect of variations in the atmospheric pressure, the ambient pressure (at the time of the aspiration) is subtracted from the lowest and highest pressure reading values obtained at each Aspiration Data Point. For example, the differential values at each Aspiration Data Point obtained from ten samples of normal calf serum are listed in Table 1. The aspiration pressure windows in future aspirations can then be calculated from these differential values by adding the ambient pressure measured at the beginning of the level sensing steps (step 1 above). The accuracy of these ranges (i.e. the differential values) will be dependant upon the number of normal samples used to establish the aspiration pressure windows. Preferably at least ten (10) samples should be used to establish the

TABLE 1

| Aspiration Pressure Windows | | |
|---|---|---|
| Aspiration Data Point | High Pressure Limit | Low Pressure Limit |
| 1 | Ambient Pressure + 60 | Ambient Pressure + 180 |
| 2 | Ambient Pressure + 60 | Ambient Pressure + 180 |
| 3 | Ambient Pressure + 120 | Ambient Pressure + 240 |
| 4 | Ambient Pressure + 170 | Ambient Pressure + 290 |
| 5 | Ambient Pressure + 210 | Ambient Pressure + 330 |
| 6 | Ambient Pressure + 240 | Ambient Pressure + 370 |
| 7 | Ambient Pressure + 280 | Ambient Pressure + 420 |
| 8 | Ambient Pressure + 300 | Ambient Pressure + 450 | aspiration pressure windows.

If any pressure reading (Aspiration Data Point) taken during the aspiration of a sample is outside of the corresponding aspiration pressure window, the sample is non-homogeneous and the aspiration is halted. For example, on the sixth pressure reading, if the ambient pressure is 512, the aspiration pressure window values according to the values in Table 1 would be from 752 (512+ 240) to 882 (512+ 370). A sample pressure reading value less than 752 or greater than 882 would indicate that the sample is non-homogeneous.

After the total amount of sample desired has been aspirated, the pipettor is moved upward a short distance, preferably about 0.055 inches, so that the end of the pipette tip is within 0.125 inches below the surface of the sample. This permits some of the sample, preferably about 50 μL, to be dispensed back into the sample. Because mechanical systems have a looseness in the mechanical connections, such as slippage between gears and the like, a backlash is observed when the mechanism driving the syringe piston is reversed in direction from its former movement. For example, when approximately 50 μL of sample is dispensed back into the sample, some of the mechanical movement readjusts the tension between the parts before the syringe piston begins to move. Thus, less than 50 μL of sample is actually dispensed back into the sample.

After dispensing aspirated sample back into the sample, a short delay, preferably at least 0.5 seconds, permits much of the sample fluid clinging to the outside of the pipette tip to run off. The pipettor is then moved a short distance upward, preferably at least about 0.5 inches, at a very slow rate, preferably no more than 2.88 inches per second. This permits the removal of the pipette tip from the sample without shearing off or loosing a small amount of sample from inside the end of the pipette tip. The pipettor can then be returned to the home position at normal speed. From the home position the pipettor is moved to a new location where dispensing of the aspirated sample occurs. Alternatively, the reaction tray is moved in place of the sample container and the pipettor is again moved downward.

A sample must be at least partially liquid to be aspirated. Thus, a sample can be a liquid biological fluid such as blood, serum, plasma, urine, cerebrospinal fluid, ascites fluid, cell growth media, tissue and swab extracts, fluids resulting from sample processing in DNA cyclizers, and the like. The biological sample can contain particles such as cells and the like. The particles can also include microparticles or other small particles used in assay procedures. A sample can also be a non-biological fluid such as water samples, or any chemical or solid which can be at least dispersed in a liquid suspension.

The following examples are illustrative of the invention and are in no way to be interpreted as limiting the scope of the invention, as defined in the claims. It will be appreciated that one skilled in the art can conceive of many other devices and methods of use to which the present inventive concepts can be applied.

EXAMPLE 1

SAMPLE DETECTION BY VACUUM

The surface of a sample (level sensing) was detected according to the method of the invention described hereinabove. A vacuum was created within the pipettor shown in FIG. 6a by aspirating air into the pipettor (with a syringe) as the pipettor was moved toward the sample surface. The pressure was monitored during this process with a pressure transducer and the data was stored in the variable named "p_array". The sample was goat plasma. The pipettor control software was executed under the control of the Soft-Scope 286 Debugger program (available from Concurrent Sciences, Moscow, Id.). This software package has the ability to monitor execution of the program and examine the values of variables during processing. After level sensing was completed, the first 30 pressure readings were determined by examining the values stored in the "p_array". A slight delay exists between each pressure reading due to the processing of the data by the computer. The length of this delay is dependent upon the software and computer hardware. A longer delay may be incorporated into the software if desired. The reading-number and pressure obtained are tabulated in Table 2.

The values in Table 2 are 10-bit binary where full scale vacuum (−1 psi) has a value of 1023 and full scale pressure (+1 psi) has a value of 0. The change in pressure at reading number 14 indicates that the surface has been reached, i.e. the tip of the pipettor has touched the sample surface. Immediately, the pipettor's movement was halted and the aspiration was stopped.. The pressure within the pipettor then return to equilibrium with ambient pressure.

These data verified the ability of the system to detect the surface of the sample while drawing a vacuum (i.e. aspirating air). The pressure values were saved during level sensing. The vacuum spike occurred when the sample was contacted. The data are graphed in FIG. 1, wherein pressure (+1 psi to −1 psi represented as 10-bit binary) is plotted against pressure readings.

EXAMPLE 2

ASPIRATION PRESSURE TEST WITH NORMAL CALF SERUM

The aspiration pressure windows were verified using normal calf serum as follows. Ten samples of normal calf serum were individually aspirated and the pipettor aspiration pressure data was saved. All ten samples were visually verified to contain no foam, bubbles, dots or other non-homogeneity. All ten samples were level sensed within 0.125 (⅛) inches of the sample surface, and thus fell within the allowed window of 0.125 inches from the sample surface. The aspiration data from all ten samples is summarized in Table 3. A representative sample is graphed in FIG. 2, wherein pressure (+1 psi to −1 psi represented as 10-bit binary) is plotted against aspiration data points. One calf serum sample, shown as the solid line between closed squares, was plotted. Also plotted was the low limit windows, graphed as the solid line between crosses, and the high limit windows, shown as the solid line between asterisks.

TABLE 2

| Reading Number | Pressure Value | Reading Number | Pressure Value | Reading Number | Pressure Value |
| --- | --- | --- | --- | --- | --- |
| 1 | 575 | 11 | 576 | 21 | 582 |
| 2 | 579 | 12 | 575 | 22 | 583 |
| 3 | 579 | 13 | 592 | 23 | 582 |
| 4 | 578 | 14 | 679 | 24 | 583 |
| 5 | 575 | 15 | 594 | 25 | 583 |
| 6 | 575 | 16 | 580 | 26 | 582 |
| 7 | 575 | 17 | 582 | 27 | 582 |
| 8 | 574 | 18 | 582 | 28 | 582 |
| 9 | 575 | 19 | 582 | 29 | 582 |
| 10 | 575 | 20 | 582 | 30 | 582 |

TABLE 3

| SAMPLE No. | Aspiration Data Points | | | | | | | | |
| --- | --- | --- | --- | --- | --- | --- | --- | --- | --- |
| | 0* | 1 | 2 | 3 | 4 | 5 | 6 | 7 | 8 |
| 1 | 582 | 718 | 718 | 771 | 821 | 859 | 893 | 925 | 949 |
| 2 | 584 | 709 | 717 | 768 | 816 | 856 | 893 | 925 | 949 |

TABLE 3-continued

| SAMPLE No. | Aspiration Data Points | | | | | | | | |
|---|---|---|---|---|---|---|---|---|---|
| | 0* | 1 | 2 | 3 | 4 | 5 | 6 | 7 | 8 |
| 3 | 583 | 709 | 708 | 769 | 819 | 857 | 893 | 925 | 951 |
| 4 | 581 | 710 | 708 | 771 | 817 | 858 | 893 | 925 | 950 |
| 5 | 583 | 712 | 712 | 773 | 822 | 861 | 898 | 928 | 954 |
| 6 | 583 | 717 | 717 | 771 | 817 | 856 | 893 | 925 | 950 |
| 7 | 583 | 709 | 709 | 774 | 821 | 861 | 896 | 926 | 952 |
| 8 | 583 | 710 | 710 | 773 | 821 | 861 | 895 | 929 | 952 |
| 9 | 584 | 706 | 710 | 770 | 816 | 857 | 893 | 924 | 949 |
| 10 | 584 | 712 | 712 | 775 | 821 | 861 | 897 | 928 | 955 |

*Ambient Pressure

EXAMPLE 3

DETECTION OF FOAM DURING ASPIRATION

The effect of foam on the surface of the sample was tested as follows. Three samples of normal calf serum each were pipetted into separate containers. All three samples were visually verified to contain no foam, bubbles, clots or other non-homogeneity. Foam was created in each sample by vigorously shaking the test sample. The fluid level was sensed according to the method of the invention described hereinabove. All three samples which contained foam resulted in a sample surface detected at the surface of the foam. However, these samples were later rejected on the basis of aspiration pressure data. The aspiration data from all three samples is summarized in Table 4. The data from one of the calf serum samples containing foam (shown as the solid line between closed squares) is graphed in FIG. 3, wherein pressure (+1 psi to −1 psi represented as 10-bit binary) is plotted against aspiration data points. Also plotted was the low limit windows, graphed as the solid line between crosses, and the high limit windows, shown as the solid line between asterisks.

EXAMPLE 4

DETECTION OF BUBBLES DURING ASPIRATION

The effect of large bubbles on the surface of the sample was tested as follows. Three samples of normal calf serum each were pipetted into separate containers. All three samples were visually verified to contain no foam, bubbles, dots or other non-homogeneity. Large bubbles were created in each test sample by blowing air on the surface of the sample using a pasteur pipet and a dropper bulb. The fluid level of each sample was then sensed according to the method of the invention described hereinabove. The aspiration data from all three samples is summarized in Table 5. It was found that the first two samples with bubbles were correctly level sensed, i.e. the bubbles present in each of these two samples had no effect on the level sense. Apparently, the pipette tip broke the bubbles as the pipettor moved toward the sample surface.

TABLE 4

| SAMPLE No. | Aspiration Data Points | | | | | | | | |
|---|---|---|---|---|---|---|---|---|---|
| | 0* | 1 | 2 | 3 | 4 | 5 | 6 | 7 | 8 |
| 1 | 582 | 825 | 752 | ** | | | | | |
| 2 | 582 | 823 | 757 | ** | | | | | |
| 3 | 582 | 839 | 758 | ** | | | | | |

TABLE 4-continued

| SAMPLE No. | Aspiration Data Points | | | | | | | | |
|---|---|---|---|---|---|---|---|---|---|
| | 0* | 1 | 2 | 3 | 4 | 5 | 6 | 7 | 8 |

*Ambient Pressure
**The sample was rejected on the basis of the initial aspiration data point and aspiration was halted.

TABLE 5

| SAMPLE No. | Aspiration Data Points | | | | | | | | |
|---|---|---|---|---|---|---|---|---|---|
| | 0* | 1 | 2 | 3 | 4 | 5 | 6 | 7 | 8 |
| 1 | 584 | 728 | 728 | 789 | 838 | 879 | 913 | 944 | 971 |
| 2 | 583 | 712 | 712 | 774 | 819 | 861 | 896 | 926 | 953 |
| 3 | 583 | 584 | 582 | ** | | | | | |

*Ambient Pressure
**The sample was rejected on the basis of the initial aspiration data point and aspiration was halted.
crosses, and the high limit windows, shown as the solid line between asterisks.

TABLE 6

| SAMPLE No. | Aspiration Data Points | | | | | | | | |
|---|---|---|---|---|---|---|---|---|---|
| | 0* | 1 | 2 | 3 | 4 | 5 | 6 | 7 | 8 |
| 1 | 582 | 1020 | 1022 | ** | | | | | |
| 2 | 578 | 937 | 699 | ** | | | | | |
| 3 | 577 | 1020 | 1020 | ** | | | | | |

*Ambient Pressure
**The sample was rejected on the basis of the initial aspiration data point and aspiration was halted.

The bubbles of the third sample hindered the sample surface level sense. The bubbles and not the sample surface were detected when the bubbles were contacted by the pipettor. This sample was rejected on the basis of the aspiration pressure data. The third sample aspiration data is graphed in FIG. 4 (shown as the solid line between closed squares), wherein pressure (+1 psi to −1 psi represented as 10-bit binary) is plotted against aspiration data points. Also plotted was the low limit windows, graphed as the solid line between

EXAMPLE 5

DETECTION OF CLOTS DURING ASPIRATION

A test was performed in order to verify the ability of the method of the invention to detect clots in a test sample. Clots were simulated by partially mixing a non-dairy creamer with water creating small lumps. Three attempts were made to aspirate this mixture by the method of the invention described hereinabove. The aspiration pressure data is summarized in Table 6.

Figure 5:
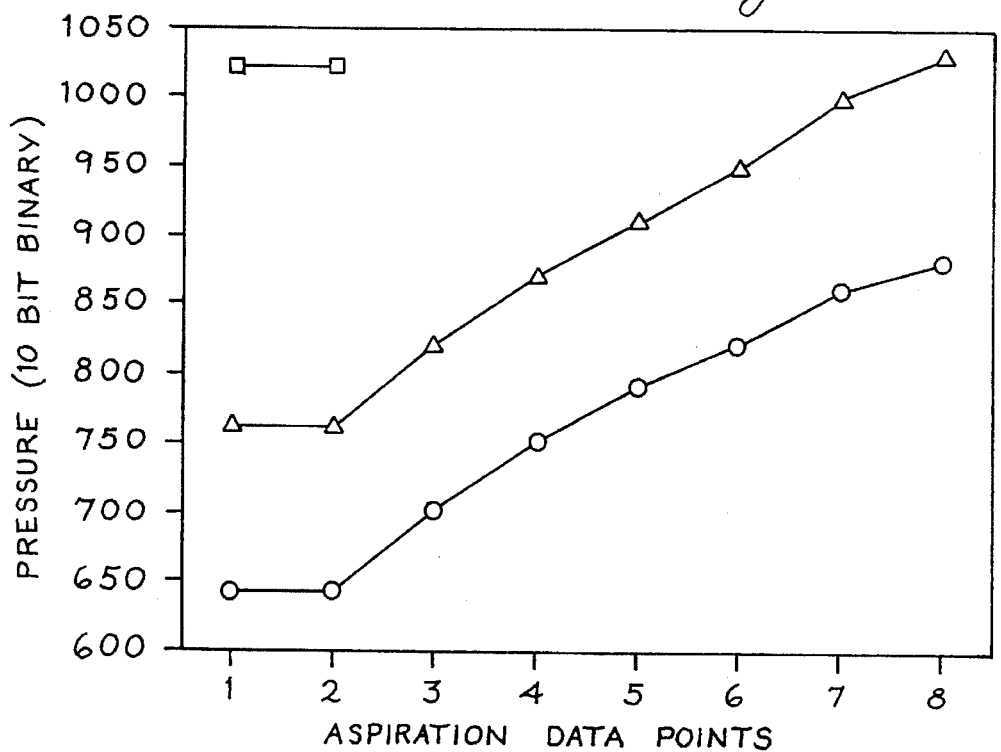
FIG. 5 is a graph of a sample of water containing a non-dairy creamer to simulate clots in the sample using the fluid level sensing and aspiration method of this invention to aspirate 1000 μL of sample, wherein Pressure (+1 psi to −1 psi represented as 10 bit binary) is plotted against Aspiration Data Points. At least one of the measured pressure values is outside a predetermined aspiration pressure window indicating a heterogeneity in the sample, i.e. the presence of a clot.

All three samples were rejected on the basis of the initial aspiration data point. The first and third samples also were out of limits on the steady state pressure following the initial aspiration. FIG. 5 is a graph of a representative sample (shown as the solid line between closed squares), wherein pressure (+1 psi to −1 psi represented as 10-bit binary) is plotted against aspiration data points. Also plotted was the low limit windows, graphed as the solid line between crosses, and the high limit windows, shown as the solid line between asterisks.

The embodiments described and the alternative embodiments presented are intended as examples rather than as limitations. Thus, the description of the invention is not intended to limit the invention to the particular embodiments disclosed, but it is intended to encompass all equivalents and subject matter within the spirit and scope of the invention as described above and as set forth in the following claims.

What is claimed is:

1. A method of detecting non-homogeneity in a fluid sample comprising:
   a. determining ambient air pressure within a pipettor as a baseline pressure reading;
   b. aspirating air into said pipettor as said pipettor is moving towards a fluid sample in a container;
   c. monitoring the air pressure in said pipettor to indicate the surface level of said sample in said container by a change in said air pressure;
   d. immersing the pipettor in said sample and aspirating a volume of said sample from the container into the pipettor;
   e. measuring the air pressure within the pipettor immediately after said aspiration of step (d) and after the pressure reaches a steady state;
   f. comparing the measured pressures of step (e) to predetermined aspiration pressure windows; and
   g. observing pressure values falling outside said windows.

2. The method of claim 1 wherein said non-homogeneity in the sample is a bubble.

3. The method of claim 1 wherein said non-homogeneity in the sample is a foamy layer.

4. The method of claim 1 wherein said non-homogeneity in the sample is a clot.

5. A method of detecting non-homogeneity in a fluid sample comprising:
   a. determining ambient air pressure within a pipettor as a baseline pressure reading;
   b. immersing the pipettor into a fluid sample and aspirating a volume of said sample into the pipettor;
   c. measuring the air pressure within the pipettor immediately after said aspiration of step (b) and after the pressure reaches a steady state;
   d. comparing the measured pressures of step (c) to predetermined aspiration pressure windows; and
   e. observing pressure values falling outside said windows,

* * * * *